(12) United States Patent
Park

(10) Patent No.: US 11,000,402 B2
(45) Date of Patent: May 11, 2021

(54) TREATMENT FOR VESICOVAGINAL FISTULA

(71) Applicant: RESTORE HEALTH, INC., Brooklyn, NY (US)

(72) Inventor: Joonhee Park, Brooklyn, NY (US)

(73) Assignee: Restore Health, Inc., Brooklyn, NY (US)

( * ) Notice: Subject to any disclaimer, the term of this patent is extended or adjusted under 35 U.S.C. 154(b) by 62 days.

(21) Appl. No.: 15/691,406

(22) Filed: Aug. 30, 2017

(65) Prior Publication Data

US 2017/0360594 A1    Dec. 21, 2017

Related U.S. Application Data

(63) Continuation of application No. PCT/US2016/022565, filed on Mar. 16, 2016.

(60) Provisional application No. 62/135,585, filed on Mar. 19, 2015.

(51) Int. Cl.
| | |
|---|---|
| *A61F 5/455* | (2006.01) |
| *A61F 2/00* | (2006.01) |
| *A61F 5/448* | (2006.01) |
| *A61F 5/449* | (2006.01) |
| *A61F 5/445* | (2006.01) |

(52) U.S. Cl.
CPC .......... *A61F 5/4553* (2013.01); *A61F 2/0009* (2013.01); *A61F 5/445* (2013.01); *A61F 5/448* (2013.01); *A61F 5/449* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,483,079 | A * | 9/1949 | Williams | A61F 5/455 604/329 |
| 3,116,734 | A * | 1/1964 | Terman | A61F 5/455 604/329 |
| 4,681,572 | A * | 7/1987 | Tokarz | A61B 1/307 600/574 |
| 5,827,248 | A * | 10/1998 | Crawford | A61F 5/4553 604/328 |

(Continued)

FOREIGN PATENT DOCUMENTS

| | | |
|---|---|---|
| CA | 2579454 A1 | 6/2006 |
| CN | 103705331 A | 4/2014 |

(Continued)

OTHER PUBLICATIONS

International Preliminary Report on Patentability dated Sep. 19, 2017 in International Application No. PCT/US2016/022565, 6 pages.

(Continued)

*Primary Examiner* — Guy K Townsend
(74) *Attorney, Agent, or Firm* — Baker Botts L.L.P.

(57) ABSTRACT

The present invention relates to methods and compositions for the treatment of vesicovaginal fistula. It is based, at least in part, on the discovery that a menstrual cup may be used to collect urine and decrease or prevent urine leakage in certain women having vesicovaginal fistula and, in some cases, the menstrual cup was observed to at least partially occlude the fistula and permit normal micturition.

11 Claims, 7 Drawing Sheets

(56) References Cited

U.S. PATENT DOCUMENTS

Figure 1:
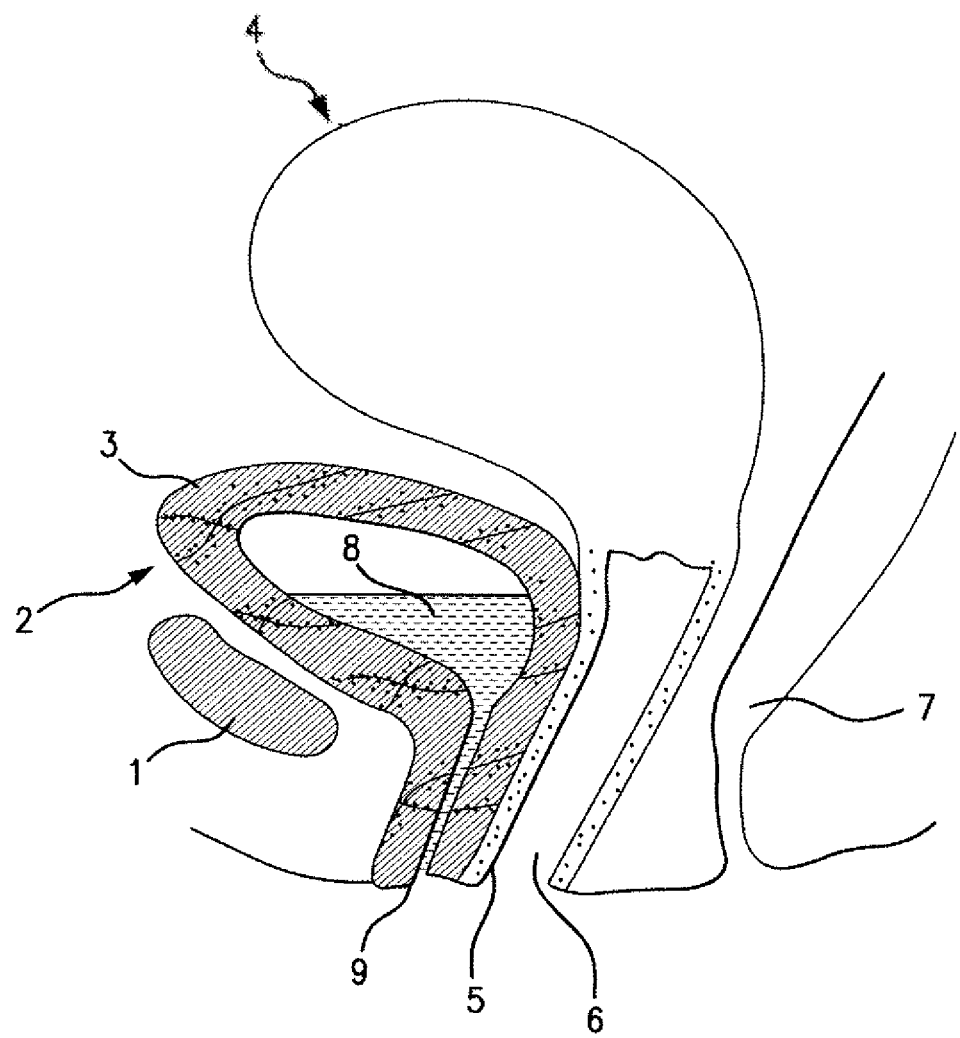

| | | | | |
|---|---|---|---|---|
| 8,740,766 B2* | 6/2014 | Rosen | A61B 17/12099 | 600/29 |
| 8,740,767 B2* | 6/2014 | Rosen | A61B 17/12 | 600/29 |
| 9,585,647 B2* | 3/2017 | Clark | A61B 17/0057 | 604/330 |
| 9,707,067 B2* | 7/2017 | Rosen | A61F 2/0009 | |
| 10,617,503 B2* | 4/2020 | Rosen | A61B 17/12099 | 604/330 |
| 2002/0049453 A1* | 4/2002 | Nobles | A61B 17/0057 | 606/139 |
| 2007/0049879 A1* | 3/2007 | Gutierrez | A61F 5/4553 | 604/330 |
| 2007/0128174 A1* | 6/2007 | Kleinsek | A61P 25/28 | 424/93.7 |
| 2008/0051831 A1* | 2/2008 | Deal | A61B 17/12099 | 606/213 |
| 2008/0200888 A1* | 8/2008 | Gooch | A61F 5/4553 | 604/330 |
| 2011/0054492 A1* | 3/2011 | Clark | A61B 17/0057 | 606/139 |
| 2011/0081323 A1* | 4/2011 | Kleinsek | A61P 1/04 | 424/93.7 |
| 2013/0138135 A1* | 5/2013 | Rosen | A61F 2/0022 | 606/197 |
| 2013/0144112 A1* | 6/2013 | Rosen | A61F 2/0031 | 600/29 |
| 2014/0275746 A1* | 9/2014 | Rosen | A61F 2/0009 | 600/31 |
| 2015/0073471 A1* | 3/2015 | Clark | A61B 17/0057 | 606/213 |
| 2017/0281325 A1* | 10/2017 | Rosen | A61F 2/0027 | 604/330 |
| 2017/0360594 A1* | 12/2017 | Park | A61F 5/4553 | 604/330 |
| 2020/0229913 A1* | 7/2020 | Rosen | A61F 2/0022 | 604/330 |

FOREIGN PATENT DOCUMENTS

| | | |
|---|---|---|
| CN | 103705332 A | 4/2014 |
| CN | 204581650 U | 8/2015 |
| CN | 106039432 A | 10/2016 |
| GB | 2 425 260 A | 10/2006 |
| WO | WO 2006/058409 A1 | 6/2006 |
| WO | WO 2014/056257 A1 | 4/2014 |
| WO | WO 2014/056258 A1 | 4/2014 |

OTHER PUBLICATIONS

International Search Report and Written Opinion dated Jun. 9, 2016 in International Application No. PCT/US2016/022565, 8 pages.

* cited by examiner

TREATMENT FOR VESICOVAGINAL FISTULA

CROSS REFERENCE TO RELATED APPLICATION

This application is a continuation of International Application Serial No. PCT/US2016/022565, filed Mar. 16, 2016, which claims priority to U.S. Provisional Application No. 62/135,585, filed Mar. 19, 2015, each of which is incorporated herein by reference in its entirety and to each of which priority is claimed.

1. INTRODUCTION

The present invention relates to compositions and methods for treating vesicovaginal fistula.

2. BACKGROUND OF THE INVENTION

Obstetric fistula is a communication, or channel, between the vagina and either the bladder ("vesicovaginal fistula") or rectum ("rectovaginal fistula"). It may arise as a result of prolonged obstructed labor or rape. Obstetric fistula has a higher incidence in low-income countries with fewer opportunities for surgical correction. According to Biadgilign et al. (2013, Reproductive Health 10:14), 10.6 per 1000 parous women in Ethiopia have experienced obstetric fistula.

Vesicovaginal fistula ("VVF") results in leakage of urine through the vagina and manifests as incontinence. VVF has been reported to have a number of psychosocial consequences, including depression, feelings of shame, social and familial ostracism, and even divorce (Alio et al., 2011, Arch. Gynecol. Obstet. 284(2):371-378; Farid et al., 2013, J. Coll. Physicians Surg. Pak. 23(10):828-829). As many of the women suffering from VVF have limited or no access to surgical repair, there is a need for non-surgical treatment options.

Menstrual cups are known in the art. These are flexible cups that can be placed in the vaginal canal in order to collect menstrual fluid. Commercially available menstrual cups include the DivaCup®, the Mooncup®, the Instead Softcup™, the Ladycup, and the Lunette menstrual cup, among others. Patents and patent applications describing menstrual cups include U.S. Pat. No. 5,827,248 to Crawford, Canadian Patent Application No. 2,579,454 to Chambers and Pickering, and International Patent Application Publication No. WO2006/058409 to Diva International.

3. SUMMARY OF THE INVENTION

The present invention relates to methods and compositions for the treatment of VVF. It is based, at least in part, on the discovery that a menstrual cup may be used to collect urine and decrease or prevent urine leakage in certain women having VVF and, in some cases, the menstrual cup was observed to at least partially occlude the fistula and permit normal micturition.

In various embodiments, the present invention provides for a method of treating VVF comprising placing a vaginal cup in the vaginal canal. In non-limiting subsets of embodiments, the vaginal cup, situated in the vaginal canal between the VVF and the entrance to the vagina, may collect urine and decrease or prevent urine leakage from the vagina. In various non-limiting embodiments, the vaginal cup, situated in the vaginal canal, may at least partially occlude the fistula and permit voiding by micturition through the urethra.

In a subset of embodiments, the vaginal cup is a menstrual cup such as those known in the art, but the invention is not limited to such menstrual cups and their uses. In non-limiting subsets of embodiments, the vaginal cup may have a reversible means of occlusion that allows periodic drainage of urine without requiring removal of the device from the vagina. In non-limiting subsets of embodiments, the dimension of the vaginal cup may be elongated to increase the likelihood that it may occlude the fistula in a subject having a VVF. In non-limiting subsets of embodiments, the vaginal cup may comprise means to connect to a urine collection bag which, for example, may be reversibly strapped to a leg of the subject.

FIG. 1 is a diagram showing normal anatomy of the female pelvic cavity. The pubic symphysis 1 serves as the anterior landmark and the rectum 7 is the posterior landmark in the diagram. The bladder 2 is filled with urine 8 and the bladder wall 3 is next to the vaginal wall 5. The uterus 4 is located above the bladder. The urethra is structure 9. Of note, the invention may also be used in a female from whom the uterous and/or cervix and/or a portion of the vagina has been removed.

Figure 2:
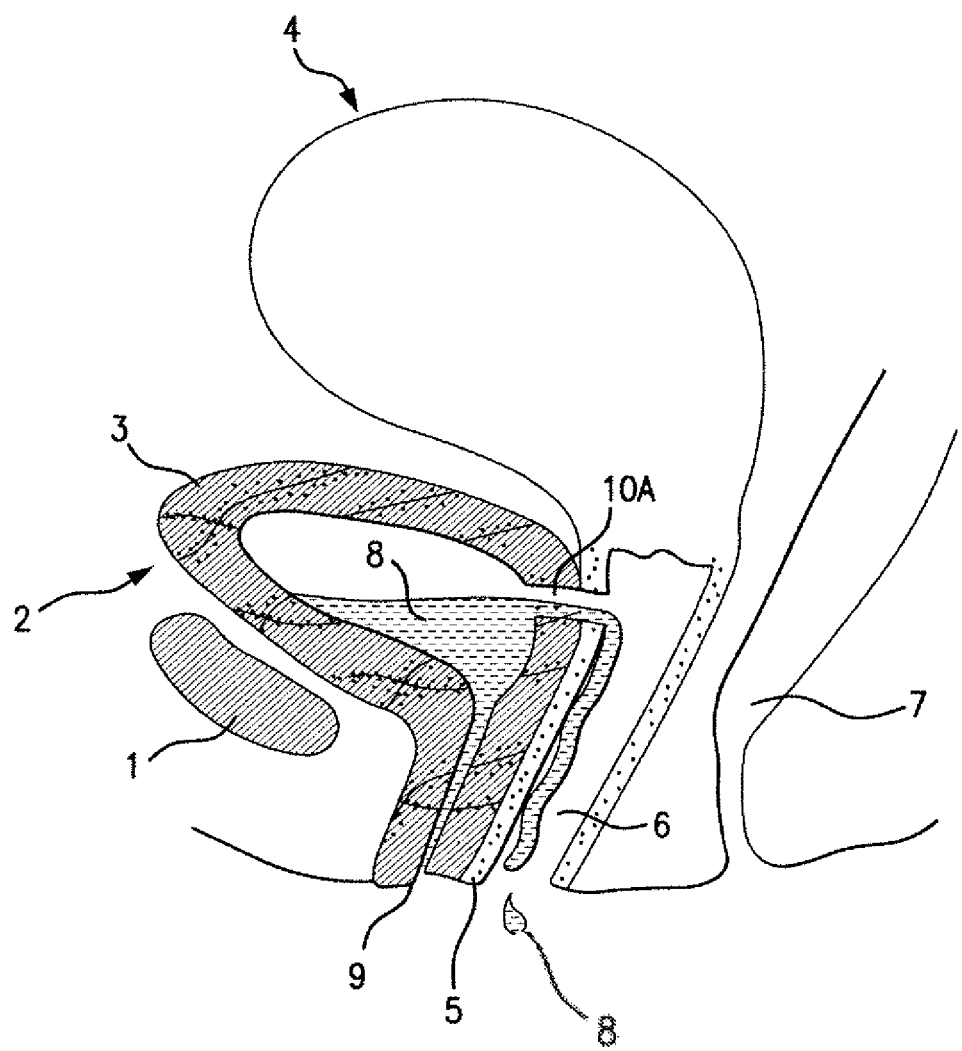

FIG. 2 is a diagram showing a VVF 10 connecting the bladder 2 and the vaginal canal 6, which results in leakage of urine 8 from the vagina canal. The VVF is located high in the vaginal wall, meaning closer to the cervix or the vaginal apex than to the vaginal entrance.

Figure 3:
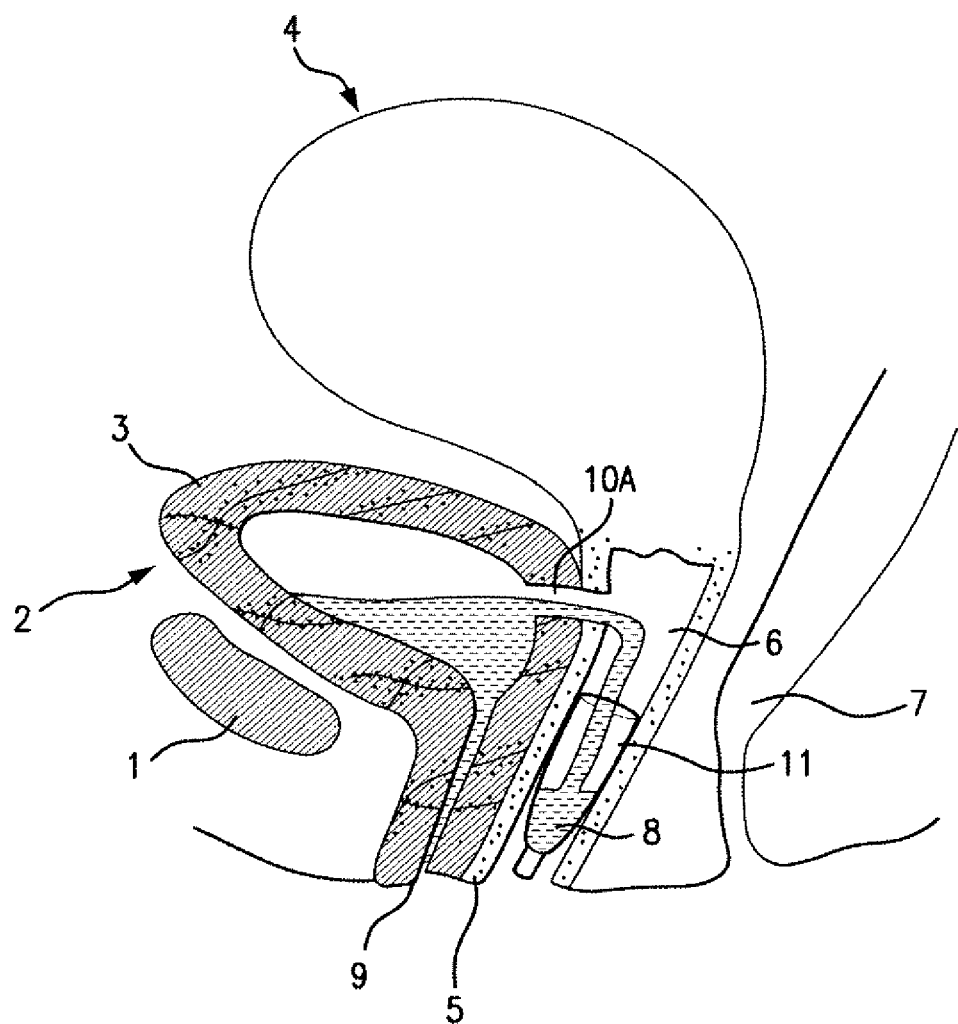

FIG. 3 is a diagram showing a vaginal cup 11 positioned in the vaginal canal 6 below the fistula 10A ("below" meaning between the VVF and the vaginal entrance) where it can collect urine 8 that has leaked through the fistula.

Figure 4:
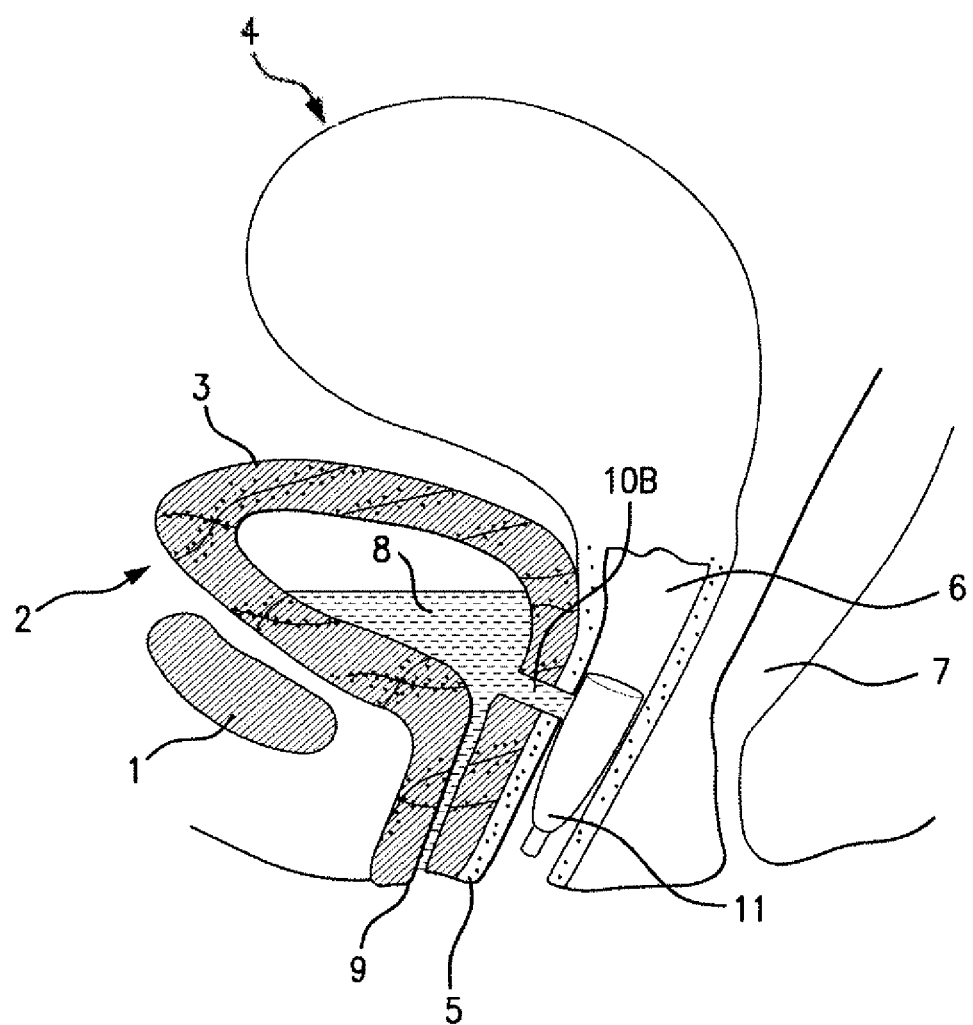

FIG. 4 is a diagram showing a VVF JOB located lower in the vaginal wall relative to the VVF 10A shown in FIGS. 2 and 3 ("lower" meaning closer to the vaginal entrance). A vaginal cup 11 positioned in the vaginal canal 6 at least partially or completely occludes the fistula and allows urine to accumulate in the bladder 8. In some instances, a subject in whom a vaginal cup at least partially or completely occludes the fistula may be able to void via her urethra, although sometimes the urethra is damaged or otherwise occluded, making voiding difficult or practicably impossible, and accumulated urine may be released by either draining the cup (for example, via an opening in the cup) or removing the cup (for example, and un-occluding the fistula).

FIG. 5A-F. (A) Side view of vaginal cup 12A having an open top end with a rim 13A, a closed bottom end with a stem 14A, and an outer surface 21A. The top diameter is 15A, the bottom diameter is 22A, and the length is 16A. (B) Side view of vaginal cup 12B having an open top end with a rim 13B, a bottom end with a stem having an open end 14B over which a cap 17 may be placed to occlude the opening, and an outer surface 21B. The top diameter is 15B, the bottom diameter is 22B, and the length is 16B. (C) Side view of vaginal cup 12C having an open top end with a rim 13C, a bottom end with a stem having an open end 14C having an attached plug 18 that may be inserted into the open end of the stem to occlude the opening, and an outer surface 21C. The top diameter is 15C, the bottom diameter is 22C, and the length is 16C. (D) Top view of vaginal cup 12A showing the interior surface of the cup 19A, the outer surface 21A, the rim 13A and the closed bottom end, showing the top of the stem 14A. The diameter is 15A. (E) Top views of vaginal cups 12B or 12C (which would be essentially the same) showing the interior surface of the cup 19B or 19C, the rim 13B or 13C, the outer surface 21B or 21C, and the top of the stem 14B or 14C and showing the opening in the stem 20.

Figure 5A:
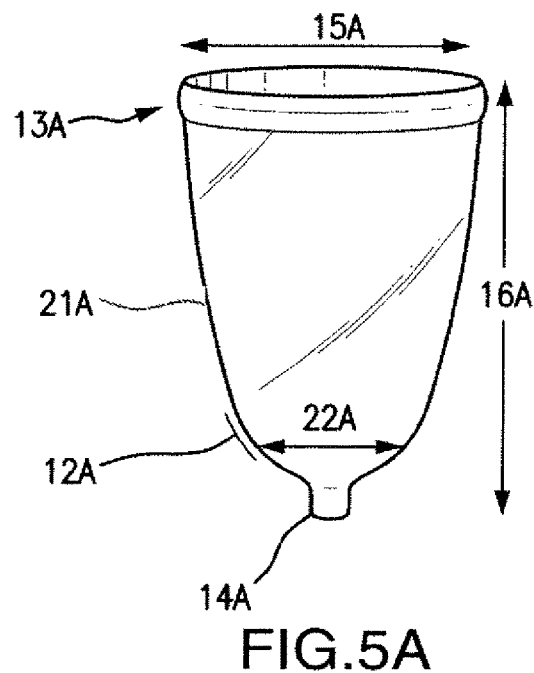
Figure 5B:
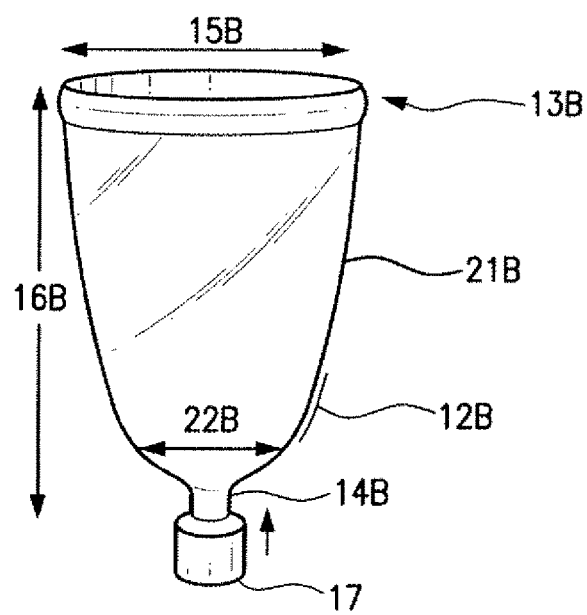
Figure 5C:
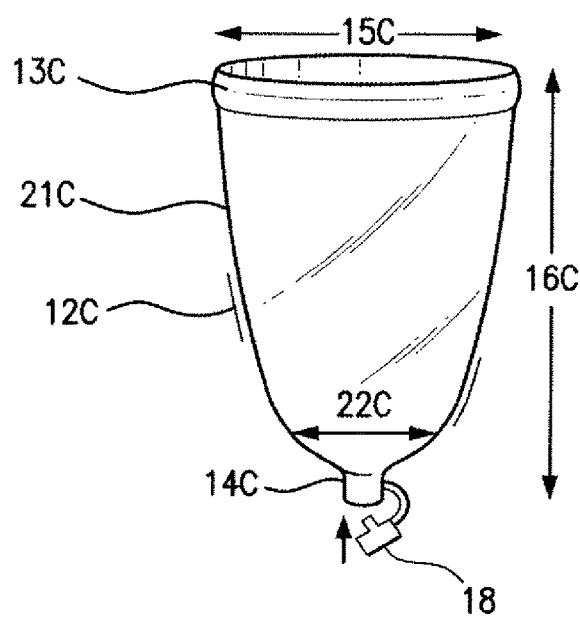
Figure 5D:
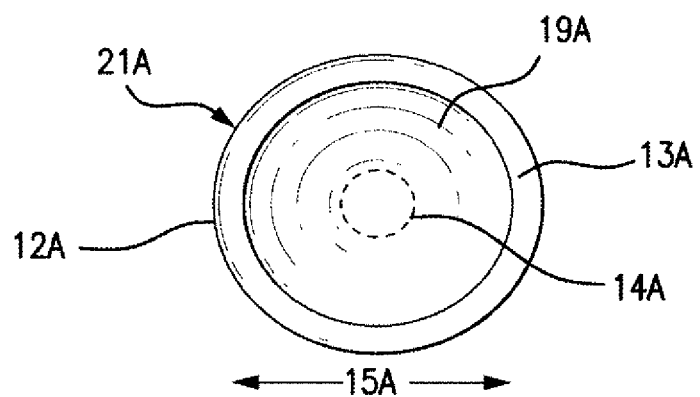
Figure 5E:
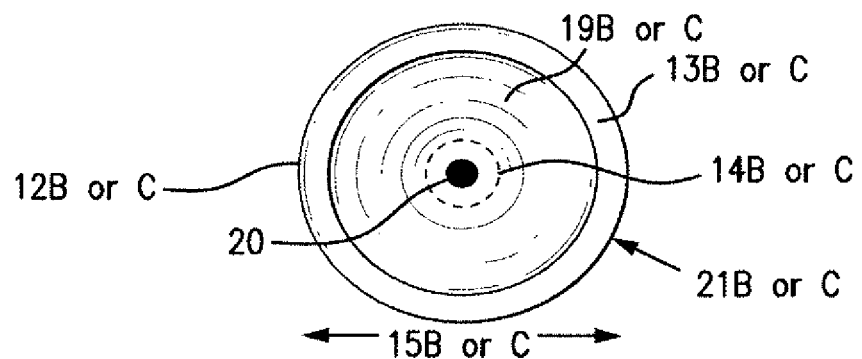

(F) Side view of the vaginal cup as depicted in FIG. 5B, wherein the stem 14B has means to connect the cup to a tubing 23 which may be connected to a collection bag 24. The present invention further envisions embodiments in which the cup does not have a stem, where optionally there is a hole in the cup which may be reversibly occluded by a stopper or a valve.

4. BRIEF DESCRIPTION OF THE DRAWINGS

FIG. 1. Schematic of normal female anatomy showing intact bladder and vaginal walls and accumulation of urine (gray) in the bladder.

FIG. 2. Schematic showing vesicovaginal fistula resulting in leakage of urine through the vaginal canal.

FIG. 3. Schematic showing vesicovaginal fistula with vaginal cup positioned in the vaginal canal to collect urine leaking through the fistula.

FIG. 4. Schematic showing vesicovaginal fistula with vaginal cup positioned in the vaginal canal to at least partly occlude the opening of the fistula into the vaginal canal, thereby allowing collection of urine in the bladder.

FIG. 5A-F. Views of vaginal cups for use according to the invention. (A) Side view of vaginal cup with closed stem. (B) Side view of vaginal cup with capped stem. (C) Side view of vaginal cup with plugged stem. (D) Top view of vaginal cup with closed stem. (E) Top view of vaginal cup with open stem. (F) Side view of vaginal cup attached to collection bag.

5. DETAILED DESCRIPTION

The vaginal cup has an outer surface, at least a portion of which contacts the vaginal wall when positioned in the vaginal canal, and an inner surface which defines a cavity. In configurations where the bottom end of the cup is closed or occluded, fluid may accumulate in the cavity of the vaginal cup.

The vaginal cup is flexible to facilitate insertion and withdrawal from the vagina.

In certain non-limiting embodiments the vaginal cup resembles a cone and has a wider top diameter and a narrower bottom diameter.

In certain non-limiting embodiments the vaginal cup resembles a tube and the top diameter and bottom diameter are approximately equal.

In certain non-limiting embodiments the rim of the vaginal cup protrudes beyond the outer surface to form a lip, which aids in retaining position when the cup is placed in the vaginal canal. In certain non-limiting embodiments the rim has greater rigidity that the body of the vaginal cup, which aids in retaining position when the cup is placed in the vaginal canal.

In certain non-limiting embodiments, the vaginal cup may have one or a plurality of small holes, for example holes having a diameter of 0.5-2 mm, located in proximity of the rim (for example, within 1 cm of the rim) to aid in insertion and withdrawal by promoting pressure equalization.

In certain non-limiting embodiments, the vaginal cup is made of a biomedical grade polymer such as, but not limited to, latex, silicone, thermoplastic polymer, or polyethylene. In a specific, non-limiting embodiment, the vaginal cup is essentially made of silicone.

In certain non-limiting embodiments the top diameter is between about 3 and 8 centimeters, or between about 4 and 6 centimeters, or between about 4 and 5 centimeters, or between about 5 and 7 centimeters, or between about 5 and 6 centimeters, or about 3 centimeters, or about 3.5 centimeters, or about 4 centimeters, or about 4.5 centimeters, or about 5 centimeters, or about 5.5 centimeters, or about 6 centimeters, or about 6.5 centimeters, or about 7 centimeters, or about 7.5 centimeters, or about 8 centimeters.

In certain non-limiting embodiments, the bottom diameter is between about 1 and 5 centimeters, or between about 1 and 3 centimeters, or about 1 centimeter, or about 1.5 centimeters, or about 2 centimeters, or about 2.5 centimeters, or about 3 centimeters, or about 3.5 centimeters, or about 4 centimeters, or about 4.5 centimeters, or about 5 centimeters.

In certain non-limiting embodiments, a vaginal cup may have dimensions wherein (i) the top diameter is between about 3 and 8 centimeters, or between about 4 and 6 centimeters, or between about 4 and 5 centimeters, or between about 5 and 7 centimeters, or between about 5 and 6 centimeters, or about 3 centimeters, or about 3.5 centimeters, or about 4 centimeters, or about 4.5 centimeters, or about 5 centimeters, or about 5.5 centimeters, or about 6 centimeters, or about 6.5 centimeters, or about 7 centimeters, or about 7.5 centimeters, or about 8 centimeters; and (ii) the bottom diameter is between about 1 and 5 centimeters, or between about 1 and 3 centimeters, or about 1 centimeter, or about 1.5 centimeters, or about 2 centimeters, or about 2.5 centimeters, or about 3 centimeters, or about 3.5 centimeters, or about 4 centimeters, or about 4.5 centimeters, or about 5 centimeters.

In certain non-limiting embodiments, the length of the vaginal cup is between about 4 and 12 centimeters, or between about 5 and 10 centimeters, or between about 6 and 10 centimeters, or about 4 centimeters, or about 4.5 centimeters, or about 5 centimeters, or about 5.5 centimeters, or about 6 centimeters, or about 6.5 centimeters, or about 7 centimeters, or about 7.5 centimeters, or about 8 centimeters, or about 8.5 centimeters, or about 9 centimeters, or about 9.5 centimeters, or about 10 centimeters, or about 10.5 centimeters, or about 11 centimeters, or about 11.5 centimeters, or about 12 centimeters, where the stem may account for between about 0.5 and 3 centimeters or between about 0.5 and 2 centimeters or about 0.5 centimeters, or about 1 centimeter, or about 1.5 centimeters, or about 2 centimeters, or about 2.5 centimeters, or about 3 centimeters, of such length. In certain non-limiting embodiments a vaginal cup having a longer length, for example a length greater than 7 centimeters or greater than 7.5 centimeters or greater than 8 cm (or greater than 6.5 centimeters excluding the stem or greater than 7 centimeters excluding the stem) may be chosen for a patient having a VVF located higher in the vaginal wall (i.e., closer to the cervix).

In certain non-limiting embodiments, a vaginal cup may have dimensions wherein (i) the top diameter is between about 3 and 8 centimeters, or between about 4 and 6 centimeters, or between about 4 and 5 centimeters, or between about 5 and 7 centimeters, or between about 5 and 6 centimeters, or about 3 centimeters, or about 3.5 centimeters, or about 4 centimeters, or about 4.5 centimeters, or about 5 centimeters, or about 5.5 centimeters, or about 6 centimeters, or about 6.5 centimeters, or about 7 centimeters, or about 7.5 centimeters, or about 8 centimeters; (ii) the bottom diameter is between about 1 and 5 centimeters, or between about 1 and 3 centimeters, or about 1 centimeter, or about 1.5 centimeters, or about 2 centimeters, or about 2.5 centimeters, or about 3 centimeters, or about 3.5 centimeters, or about 4 centimeters, or about 4.5 centimeters, or about 5 centimeters; and (iii) the length is between about 4 and 12 centimeters, or between about 5 and 10 centimeters, or between about 6 and 10 centimeters, or about 4 centimeters, or about 4.5 centimeters, or about 5 centimeters, or about 5.5 centimeters, or about 6 centimeters, or about 6.5 centimeters, or about 7 centimeters, or about 7.5 centimeters, or about 8 centimeters, or about 8.5 centimeters, or about 9 centimeters, or about 9.5 centimeters, or about 10 centimeters, or about 10.5 centimeters, or about 11 centimeters, or about 11.5 centimeters, or about 12 centimeters, where the stem may account for between about 0.5 and 3 centimeters or between about 0.5 and 2 centimeters or about 0.5 centimeters, or about 1 centimeter, or about 1.5 centimeters, or about 2 centimeters, or about 2.5 centimeters, or about 3 centimeters, of such length.

In certain non-limiting embodiments the vaginal cup does not have a stem.

In certain non-limiting embodiments the vaginal cup has a stem, and the stem may be of a length and flexibility so that, when the vaginal cup is in place in the vagina, the stem protrudes from the vagina to facilitate release of urine and emptying of the cup.

Figure 5F:
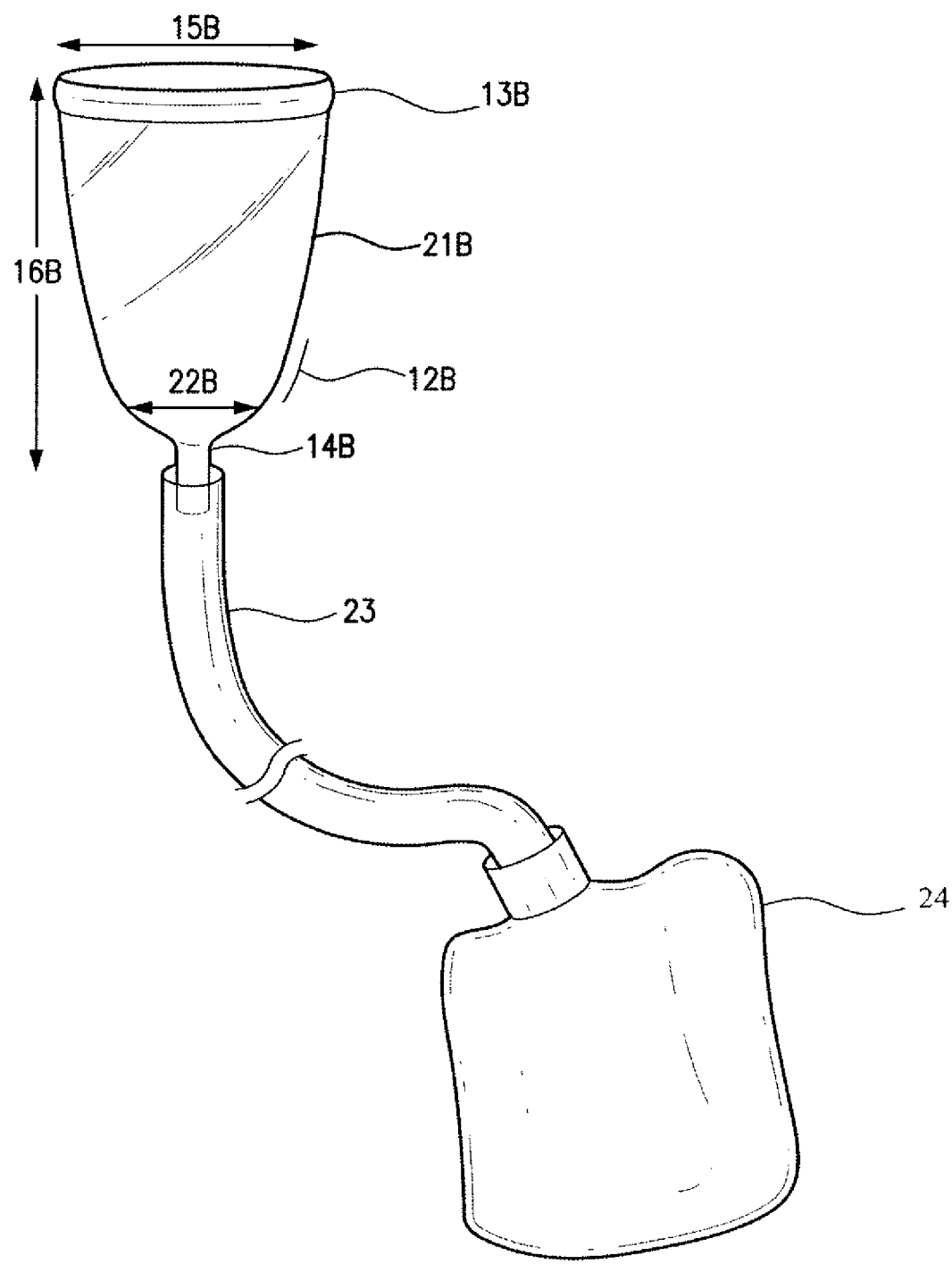

In certain non-limiting embodiments the stem may be configured to reversibly attach to a tube which connects or may be connected to a collection bag (e.g., see FIG. 5F). Medical tubing connectors are known in the art, for example but not limited to mating compatible connectors. Tubing that connects to urine collection bags are known in the art. In non-limiting embodiments a collection bag may be strapped to the leg of a subject for portability.

In certain non-limiting embodiments the vaginal cup is a menstrual cup, as known in the art, for example menstrual cups as described in U.S. Pat. No. 5,827,248 to Crawford, Canadian Patent Application No. 2,579,454 to Chambers and Pickering, and International Patent Application Publication No. WO2006/058409 to Diva International, and or a commercially available menstrual cup such as the Diva-Cup®, the Mooncup®, the Instead Softcup™, the Ladycup, or the Lunette menstrual cup.

In certain non-limiting embodiments, the present invention provides for a method of treating a subject having a VVF comprising placing, in the vaginal canal of the subject, a vaginal cup as described above, wherein placement of the vaginal cup in the vaginal canal results in collection of urine.

The vaginal cup may be placed by a physician but the subject is desirably taught how to insert and remove the vaginal cup herself. The vaginal cup is inserted by folding the cup by pressing facing portions of the rim together and then inserting it into the vagina using essentially the same technique as used for the insertion of a menstrual cup.

In certain non-limiting embodiments, the present invention provides for a method of treating a subject having a VVF comprising placing, in the vaginal canal of the subject, a vaginal cup as described above, wherein placement of the vaginal cup in the vaginal canal results in collection of urine and decreases or prevents leakage of urine from the vaginal canal to the exterior of the subject.

In certain non-limiting embodiments, the present invention provides for a method of treating a subject having a VVF comprising placing, in the vaginal canal of the subject, a vaginal cup as described above, wherein placement of the vaginal cup in the vaginal canal results in at least partial occlusion of the VVF. In a non-limiting subset of such embodiments, the vaginal cup essentially completely occludes the VVF.

In certain non-limiting embodiments, the present invention provides for a method of treating a subject having a VVF comprising placing, in the vaginal canal of the subject, a vaginal cup as described above, wherein placement of the vaginal cup in the vaginal canal results in a decrease or prevention of leakage of urine from the vaginal canal to the exterior and an improvement in the ability of the subject to void urine through the urethra.

In certain non-limiting embodiments, the method comprises emptying the vaginal cup after at least 2 hours, or after at least 4 hours, or after at least 6 hours, or after at least 12 hours, or after at least 24 hours. The vaginal cup may be emptied by either removing the cup, or by uncapping or unplugging the cup.

In certain non-limiting embodiments, the method comprises connecting the stem of the cup to a collection reservoir so that urine may flow from the cup to the collection reservoir.

In certain non-limiting embodiments, the vaginal cup may be removed from the subject about once a day or about once a week.

In certain non-limiting embodiments, where the cup at least partially or completely obstructs the VVF (thus allowing the bladder of the subject to fill), the subject may learn to approximate how long it takes for her bladder to fill (for example, by recognizing the sensation of having a fully distended bladder) before voiding through the urethra, releasing accumulated urine through the vagina cup, or releasing accumulated urine after withdrawing the vaginal cup.

As working examples, use of a Diva® menstrual cup in a small number of women with VVF resulted in reduction or correction of urine leakage, and in some instances insertion of a vaginal cup was observed to apparently occlude the fistula hole and allowed urine to collect in the wearers' bladders.

Various publications and patents are set forth herein, the contents of which are hereby incorporated by reference in their entireties.

What is claimed:

1. A method of treating a subject having a vesicovaginal fistula including an opening comprising:
   providing a removable elongate vaginal cup having an open top end with a rim, a bottom end, and a side surface extending from the rim to the bottom end,
   placing the elongate vaginal cup in a vaginal canal of the subject and locating the side surface of the elongate vaginal cup adjacent to the opening of the vesicovaginal fistula, wherein the elongate vaginal cup is configured to at least partially occlude the opening without being inserted into the opening of the vesicovaginal fistula.

2. The method of claim 1, wherein of placing the elongate vaginal cup in the vaginal canal is configured to decrease or prevent leakage of urine from the vaginal canal to an exterior of the subject.

3. The method of claim 1, further comprising emptying the elongate vaginal cup after at least 4 hours.

4. The method of claim 1, wherein the elongate vaginal cup comprises a stem and the method further comprises connecting the stem to a collection reservoir so that urine flows from the elongate vaginal cup to the collection reservoir.

5. The method of claim 1, wherein the elongate vaginal cup comprises a valve.

6. The method of claim 1, wherein the elongate vaginal cup is configured to be placed and removed by the subject.

7. The method of claim 1, wherein the elongate vaginal cup in the vaginal canal is configured to collect urine leaked from the opening of the vesicovaginal fistula.

8. The method of claim 1, wherein the elongate vaginal cup comprises a bottom diameter of least 3 cm and a top diameter of at most 4 cm.

9. The method of claim 1, wherein the elongate vaginal cup comprises a bottom diameter and a top diameter, wherein the bottom diameter dimension is at least three-fourths of the top diameter dimension.

10. The method of claim 1, wherein the side surface is nearly cylindrical in shape.

11. The method of claim 1, wherein the elongate vaginal cup is configured to fully occlude the opening of the vesicovaginal fistula.

* * * * *